(12) United States Patent
Delamarche et al.

(10) Patent No.: US 8,202,438 B2
(45) Date of Patent: Jun. 19, 2012

(54) METHOD FOR PROCESSING A SURFACE

(75) Inventors: Emmanuel Delamarche, Thalwil (CH); Matthias Geissler, Boucherville (CA)

(73) Assignee: International Business Machines Corporation, Armonk, NY (US)

( * ) Notice: Subject to any disclaimer, the term of this patent is extended or adjusted under 35 U.S.C. 154(b) by 1175 days.

(21) Appl. No.: 11/959,190

(22) Filed: Dec. 18, 2007

(65) Prior Publication Data

US 2008/0245771 A1    Oct. 9, 2008

(30) Foreign Application Priority Data

Dec. 21, 2006 (EP) ..................... 06126899

(51) Int. Cl.
*B44C 1/22* (2006.01)
*C03C 15/00* (2006.01)
*C03C 25/68* (2006.01)
*C23F 1/00* (2006.01)

(52) U.S. Cl. ................ 216/41; 216/105; 427/256

(58) Field of Classification Search ............. 216/105, 216/106, 83, 41
See application file for complete search history.

(56) References Cited

U.S. PATENT DOCUMENTS 6,001,587 A * 12/1999 Turner et al. ............. 435/41

FOREIGN PATENT DOCUMENTS

WO    WO 2005080255 A1 *  9/2005

\* cited by examiner

*Primary Examiner* — Roberts Culbert
(74) *Attorney, Agent, or Firm* — William Stock; Anne Vachon Dougherty

(57) ABSTRACT

A method for processing a surface involves depositing at least one class of enzymes (2) onto the surface (1); introducing at least a reactant (3) into an environment of the surface (1), and causing interaction between the enzymes (2) and the reactant (3), thereby to cause processing of a region of the surface (1), the processed region of the surface (1) being defined with respect to a region thereof that is proximate (4) to where the enzymes (3) have been deposited.

6 Claims, 2 Drawing Sheets

METHOD FOR PROCESSING A SURFACE

FIELD OF THE INVENTION

The present invention relates to a method for processing a surface. More particularly, the present invention relates to a method for processing a surface using enzymes.

BACKGROUND OF THE INVENTION

Micro-Fabrication

Micro-fabrication techniques are used to process surfaces and bulk materials for applications in microelectronics, optics, bio-sensing, metrology, displays and life sciences, for example. By way of such techniques, the spatially-controlled/selective removal of materials from a surface can be done. This is achieved by using techniques such as, for example, those involving etching or, alternatively, involving the local deposition of materials on a surface. Etching and deposition of materials can be done using reagents dissolved in a chemical bath, commonly referred to as wet chemistry, or what are commonly referred to as dry processes where the reagents are in gaseous form.

For the selective removal of materials from a surface, those areas where it is desired for material to remain should be protected. It has been proposed to do such protection by using lithography where an organic resist or metal layer is patterned or locally deposited on a surface. Regarding the use of resists, two techniques are typically used for their patterning. The first is electron-beam lithography where an electron beam writer is used to expose a resist with a focused beam of electrons. Exposure of the resist to electrons modifies the solubility of the resist in some solutions, which are used to transfer the electron-beam written pattern into the resist. This step is called the development step and typically the resist is made more soluble in the areas exposed to the electron beam. The second typically-used technique is photolithography, which relies on the chemical modification of a photosensitive layer by light to remove, i.e. by the use of positive tone photoresist, or prevent the removal of the photoresist, i.e. by the use of negative tone photoresist, in the areas of light exposure during a development step. Patterning of resist materials is done with several processing steps such as spin coating, baking, exposure to electrons or light, developing the exposed resist, plasma cleaning steps, and metrology of the developed resist, for example. During these steps, expensive materials such as, for example, high-purity chemicals, solvents and metals, and instruments such as, for example, mask aligners, electron-beam writers, evaporators, are used. Waste materials and chemicals are produced, which have associated safety and environmental concerns for their disposal.

After the resist has been patterned, it is used as a physical barrier against chemicals from a bath or in the gas phase to protect the underlying surface from etching. Surfaces to be processed can be large in area, for example, greater than 1 m$^2$, thus using proportional amounts of chemicals and resist—the size of such surfaces and the amount(s) of reagents used in their processing is, of course, translated into the size of the chemical baths that are used for such purposes. For such surfaces, the cost of processing equipment rises exponentially.

From the discussion above, it can be seen that micro-fabrication processes are typically based on several deposition, patterning, etching steps. For example, thin-film transistor arrays for flat panel displays are typically processed with between 30 to 60 processing steps and hard-disk drive heads may use over 250 steps, for example. As devices progress in the process flow, they become more valuable, yields diminish, and the materials and structures present on the surfaces of the devices become increasingly heterogeneous. These surfaces then have varying degrees of reactivity with chemicals in baths or in a gas phase. A layer, deposited or processed early in a process might be corroded or adversely altered in a subsequent step. Obviating such a problem may require substantial efforts for devising a processing chemistry that is specific to one type of material. If such chemistry cannot be found or implemented, fragile parts of a device must be specifically protected and additional processing steps have to be added for such a purpose. This adds to the overall cost for processing surfaces and causes reduced fabrication yields.

Wet-Etching

The transferal of a resist pattern into an underlying substrate can be done using wet chemistry, in particular, wet-etching. For this purpose, corrosive chemicals are typically used to remove material/atoms from the regions of a surface, which are not protected by the resist. Etch baths are typically large in volume, for example, they can be greater than 40 litres, contain toxic or hazardous chemicals, should be of well-defined composition, and are usually expensive because the chemicals which they contain are of a high chemical grade and the baths should be free of contaminating particulates. In some cases, such baths have limited stability and/or cannot be reused. They might have to be stirred, maintained at a specific temperature, de-aerated or a combination thereof. Reusing or disposing of etch baths is expensive. Flammable etch baths should be equipped with fire suppressing equipment depending on their volume. The CRC Handbook of Metal Etchants; Walker, P., Tarn, W. H., Eds.; CRC Press: Boca Raton, Fla., 1991, discloses that most of the common etch chemistries involve concentrated acids, combinations of acids, heated etch baths, stirring baths, toxic compounds, and/or alkaline solutions.

Baths may be sprayed and reagents may be recycled in processing tools for alleviating the consumption and waste of chemicals. Such processing tools reuse some of the reagents, the number of times of the reuse being dependent on the chemistry or purity degradation characteristics of the reagents. Such tools are typically expensive. Despite the availability of such processing tools, some micro-fabrication processes are sensitive to the history of chemicals and so reagents may not be reused. Also to be considered is that particulates tend to form and accumulate in baths, for example. Unstable baths have to typically be prepared shortly before use. Electroless deposition baths for silver (Ag) are, for example, mixed and sprayed directly onto substrates.

An introduction to micro-fabrication can be found in "Fundamentals of Micro-fabrication" by M. J. Madou, CRC Press, New York, 2002. Current reviews on micro-fabrication techniques have been given by Xia et. al in Chem. Rev. 1999, volume 99, pages 1823 to 1848 and Geissler et. al in Advanced Materials, volume 16, 2004, pages 1249 to 1269. Some of the techniques described therein provide remedies to one or several of the above-described issues by, for example, patterning surfaces directly without using resists.

Local Processing

Local processing of surfaces, i.e. the processing of a localized region or regions on a surface, has been done using a variety of scanning techniques, for example, using scanning tunneling microscopy, atomic force microscopy, and dip-pen nanolithography. These techniques use a controlled probe-surface interaction and involve serial writing. They are expensive by virtue of the: precision positioning mechanisms; micro-fabricated probes, which have a limited lifetime, and the use of specialized software. They are complex because of the extensive work that is done to develop reliable process parameters. These techniques also require several steps to be performed, such as, for example, treating the surface to be processed with a resist, writing the pattern, developing the pattern, selectively structuring the surface, and removing the resist left.

Patterning of a surface may be done using an inkjet. In this case a resist or material of interest is deposited onto a surface. This technique is versatile but lacks resolution due to the surface tension of liquids, which prevents forming droplets having a diameter below approximately 70 micrometers. Uncontrolled spreading and evaporation of inks on a surface also pose drawbacks for this technique. Viscous inks can be difficult to dispense and inkjet nozzles can be damaged by corrosive chemicals.

Laser ablation can be used to process surfaces by removing materials but this technique is limited in resolution, throughput and uses expensive lasers. Focused ion beams can be used to remove or deposit materials from or onto surfaces but this technique involves expensive equipment, must be operated under vacuum conditions, and is serial and, therefore, may be considered time-inefficient for surface-processing purposes.

Micro-contact printing is a technique for structuring surfaces. It uses a patterned elastomer, which is replicated from a mold, and that is inked and placed in contact with a surface. In the regions of contact, some of the ink transfers to the printed surface. It is used most notably to pattern self-assembled monolayers on gold (Au), silver (Ag), copper (Cu) or palladium (Pd), which are used to protect the printed areas of the metal from etchants. Despite the fact that micro-contact printing can process different-dimensioned, planar, and even curved substrates with increased accuracy compared to previously-proposed techniques, it relies on transferring the printed pattern into a surface in processing baths. Therefore, similar limitations as above-described with reference to known lithographic techniques may be encountered when micro-contact printing is used for patterning surfaces.

Examples of micro-contact printing for the patterning of surfaces are given in: Applied Physics Letter, volume 63, pages 2002 to 2004 by Whitesides et. al., Nano Letters, volume 3, 2003, pages 1449 to 1453 by Reinhoudt et. al, and Advanced Materials, volume 17, 2005, pages 1361 to 1365 by Grzybowski et. al.

Techniques have been proposed for the processing of surfaces without the use of resists or wet-etching. Examples of such techniques have been disclosed in: Nano Letters, volume 5, 2005, pages 321 to 324 by Frechet et. al, Nano Letters, volume 3, 2003, pages 1639 to 1642 by Gheber et. al and in Nature Materials, volume 4, 2005, pages 622 to 628 by Juncker et. al. Drawbacks associated with these techniques include that, being based on scanning probe microscopy methods, precision positioning techniques/features and/or the use of micro-fabricated probes make them costly. Their serial nature makes these techniques time-inefficient.

Accordingly, it is desirable to provide a method for processing a surface that mitigates and/or obviates the drawbacks associated with known surface processing techniques.

SUMMARY OF THE INVENTION

According to an embodiment of the present invention, there is provided a method for processing a surface comprising the steps of: depositing at least one class of enzymes onto the surface; introducing at least a reactant into an environment of the surface, and causing interaction between the enzymes and the reactant, thereby to cause processing of a region of the surface, the processed region of the surface being defined with respect to a region of the surface that is proximate to where the enzymes have been deposited. An embodiment of the present invention offers the advantage of selectively processing/patterning/modifying a surface without the drawbacks associated to previously-proposed methods on account of: resists and/or masks are not used for the patterning; enzyme quantities needed for coverage of a surface are much smaller than those needed for the processing materials used in previously-proposed surface processing techniques; milder etch baths or buffers are used; processing of the surface may be done in a manner that is time-efficient, wastes fewer resources/raw materials and that is relatively safer than previously-proposed surface processing techniques.

Preferably, processing of the surface comprises one of: etching of the surface and deposition of at least a depositing species on the surface. An embodiment of the present invention may be used for the subtractive patterning of a surface, that is, the interaction between the enzymes and the reactant is such that etch precursors present in the chemical bath are converted into active etching species, thereby to cause etching of the surface in a region of the surface that is defined with respect to the aforementioned proximate region. An embodiment of the present invention may also find application where additive patterning of a surface is desired, that is, it is desired to induce modification of the surface profile by deposition of a depositing species in a region of the surface that is defined with respect to the proximate region. Whether applied for additive patterning or subtractive patterning, few modifications need to be made to the implementation of an embodiment of the present invention. Thus, an embodiment of the present invention advantageously combines simplicity of implementation with versatility of application.

Desirably, in the step of causing interaction between the enzymes and the reactant, the processed region of the surface is substantially outside the proximate region. Regarding the enzymes and the reactant in an embodiment of the present invention, they may be selected to cause etching of the surface in a region of the surface that lies substantially outside the proximate region, i.e. outside the periphery of the proximate region. Thus, in the case of subtractive patterning, etching of the surface would occur outside the periphery of the proximate region. Where additive patterning is done, deposition of the depositing species would occur outside the proximate region. In this way, selective processing, in the way of patterning and/or modification, of the surface may be achieved with an embodiment of the present invention.

Preferably, the surface is selected to comprise copper (Cu), the reactants are selected to comprise hydrochloric acid (HCl) and hydrogen peroxide ($H_2O_2$) and the class of enzymes is selected to comprise horseradish peroxidase (HRP). In this case, the copper surface is protected from being etched by the $H_2O_2$ in the proximate region to where HRP has been deposited on the surface on account of the HRP reducing the $H_2O_2$.

Desirably, in the step of causing interaction between the enzymes and the reactant, the processed region of the surface is substantially in the proximate region. Regarding the enzymes and the reactant in an embodiment of the present invention, they may be selected to cause etching of the surface in a region of the surface that lies substantially within the periphery of the proximate region. Thus, for subtractive and additive patterning, etching and deposition of a depositing species, respectively, would occur within the proximate region. In this way, selectivity of how the surface is processed may be exercised without the need for substantial modification of the implementation and/or steps of an embodiment of the present invention. In this case, a preferred embodiment is where the surface is selected to comprise copper (Cu) and the class of enzymes is selected to exhibit the property of catalyzing the formation of amines.

Desirably, the spatial extension of the proximate region relative to where the enzymes have been deposited on the surface is adjustable by adjusting the concentration of the reactant, the density of the enzymes, the temperature of the environment of the surface or a combination thereof. In an embodiment of the present invention, the proximate region extends spatially outwards from where the enzymes have been deposited on the surface. Depending on how much of the surface is desired to be processed, the proximate region, for example, the extent to which it extends radially outwards from where the enzymes have been deposited on the surface, may be tailored.

Preferably, in the step of depositing the enzymes, at least another class of enzymes is additionally deposited on the surface. In an embodiment of the present invention, by the selection of different classes of enzymes, processing of the surface at different rates and/or simultaneous additive and subtractive patterning may be done. The different classes of the enzymes may be advantageously deposited in the same or different processing steps on the surface.

Desirably, in the step of depositing the enzymes, the enzymes are deposited onto the surface by micro-contact printing. In an embodiment of the present invention, the enzymes are deposited onto the surface by way of microcontact printing, thereby to avoid treatment of the enzymes by organic solvents, heat and/or ultraviolet light, which may affect the catalytic ability of the enzymes and, in the worst case scenario, render them ineffective by denaturing them.

Any disclosed embodiment may be combined with one or several of the other embodiments shown and/or described. This is also possible for one or more features of the embodiments.

BRIEF DESCRIPTION OF THE DRAWINGS

Reference will now be made, by way of example, to the accompanying drawings, in which.

DETAILED DESCRIPTION OF PREFERRED EMBODIMENTS

Figure 1:
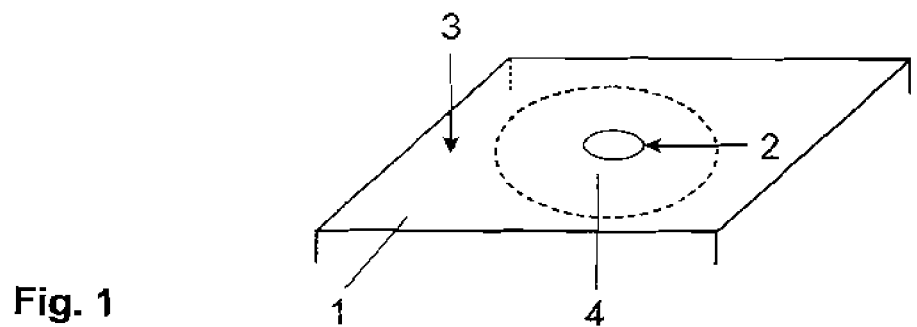
FIG. 1 schematically illustrates the principle of an embodiment of the present invention, and FIGS. 2A to 2D schematically illustrates embodiments of the present invention.

Within the description, the same reference numerals or signs have been used to denote the same parts or the like.

Reference is now made to FIG. 1, which schematically illustrates the principle of an embodiment of the present invention. As can be seen from FIG. 1, a surface 1 is processed/patterned by using enzymes 2. Specifically, at least one class of enzymes 2 is deposited onto the surface 1. At least a reactant 3 is then introduced into an environment of the surface 1 that has been modified by the deposition of enzymes 2, this typically being done in a chemical bath. In an embodiment of the present invention, the class of enzymes 2 is selected on account of exhibiting a property that the enzymes 2 interact with the reactant 3 to cause patterning of the surface 1 in a region of the surface that is defined relative to a region that is proximate to where the enzymes have been deposited, this region hereinafter also being referred to as the proximate region 4.

Reference is now made to FIGS. 2A to 2D, which schematically illustrate different embodiments of the present invention for additive or subtractive patterning of a surface 1.

Figure 2:
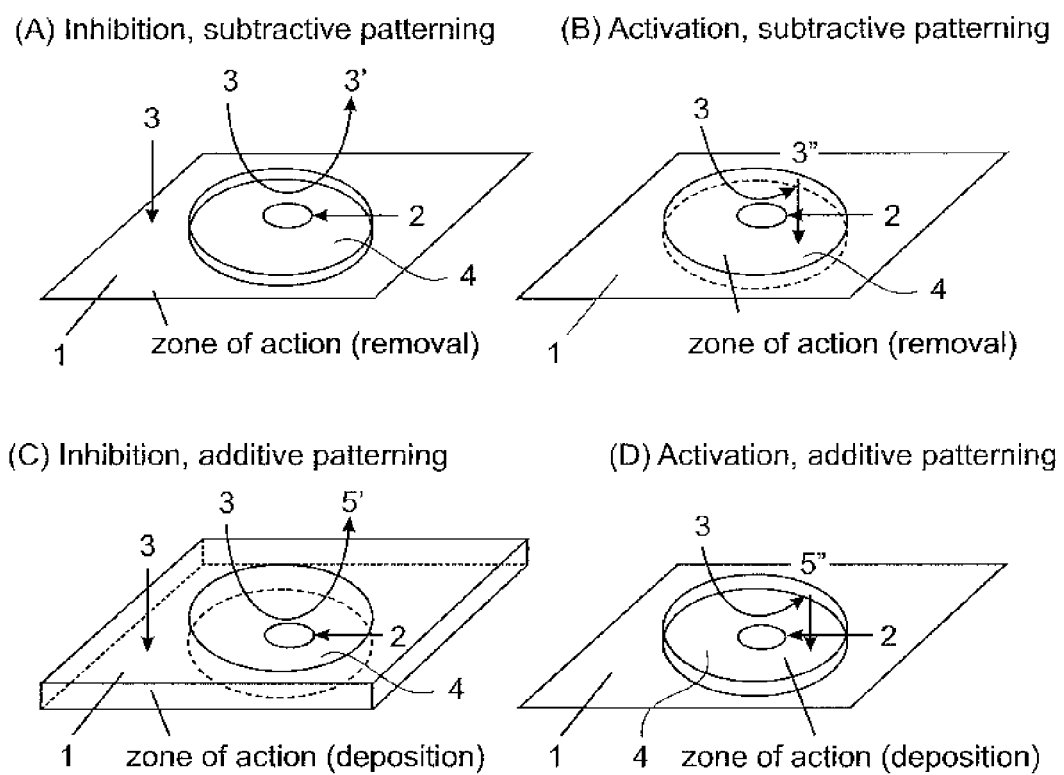

With reference now being made to FIG. 2A, in an embodiment of the present invention, the class of enzymes 2 and the reactant 3 may be chosen so as to effectuate subtractive patterning, in particular, etching of the surface 1 in a region substantially outside the proximate region 4, that is, outside the periphery of the proximate region 4. In this case, the class of the enzymes 2 is chosen to cause the reactant 3 to be converted to a deactivated species 3' in the proximate region 4. Thus, the surface 1 is only etched in a region of the surface 1 that lies outside the periphery of the proximate region 4 by the reactant 3.

With reference now being made to FIG. 2B, in an embodiment of the present invention, the class of enzymes 2 and the reactant 3 may be chosen so as to effectuate subtractive patterning, in particular, etching of the surface 1 in a region substantially within the proximate region 4, that is, inside the periphery of the proximate region 4. In this case, the class of the enzymes 2 is chosen to cause the reactant 3 to be converted to an activated species 3" in the proximate region 4. Thus, the surface 1 is only etched in a region of the surface 1 that lies within the periphery of the proximate region 4 by the reactive species 3".

Referring to FIG. 2C, in an embodiment of the present invention, the class of the enzymes 2 and the reactant 3 may be chosen to cause additive patterning of the surface 1, that is, modification of the surface 1 by deposition of a material thereon. In the case shown in FIG. 2C, the class of the enzymes 2 is chosen to cause the reactant 3 to be converted to a species 5' that is, for example, soluble, so that deposition of material does not occur in the proximate region 4 but occurs elsewhere on the surface 1 outside the periphery of the proximate region 4.

Referring to FIG. 2D, in an embodiment of the present invention, the class of the enzymes 2 is chosen to cause the reactant 3 to be converted to a depositing species 5" that is, for example, insoluble and, therefore, deposited within the periphery of the proximate region 4.

In an embodiment of the present invention, the proximate region 4 extends spatially outwards from where the enzymes 2 have been deposited on the surface 1. Depending on how much of the surface 1 is desired to be processed, the proximate region 4 and, for example, the extent to which it extends radially outwards from where the enzymes have been deposited on the surface 1 may be adjusted by adjusting the concentration of the reactant (3), the density of the enzymes (2), the temperature of the environment of the surface (1) or a combination thereof.

In an embodiment of the present invention, by the selection of different classes of enzymes 2, processing of the surface 1 at different rates and/or simultaneous additive and subtractive patterning may be done. The different classes of the enzymes 1 may be advantageously deposited in the same or different processing steps on the surface 1.

In an embodiment of the present invention, the enzymes 2 are deposited onto the surface 1 by way of micro-contact printing, thereby to avoid treatment of the enzymes by organic solvents, heat and/or ultraviolet light, which may affect the catalytic ability of the enzymes 2 and, in the worst case scenario, render them ineffective by denaturing them. Further features and/or advantages associated to using micro-contact printing for transferring the enzymes 2 onto the surface 1 include: enzymes 2 can be inked onto the surface of a micro-patterned stamp to which they adsorb to non-specifically and also the transferal of enzymes 2 from a micro-patterned stamp onto a wide variety of surfaces, including glass, metals, polymers, plastics and silicon wafers, can be done. The present invention is, of course, not limited to the use of micro-contact printing for depositing the enzymes 2 onto the surface 1, and indeed any appropriate method can be used for such a purpose.

Some of the advantages associated to the use of enzymes 2 within the context of the present invention are presented herebelow.

The diffusion profile of the enzymatic products, i.e. products of the interaction between the enzymes 2 and the reactant 3, the density and pattern geometry of the enzymes 2 on the surface 1 and the activity of the enzymes 2 can be combined to create a variety of chemical environments, the composition of which can be varied on short length scales, for example, on less than 1 micrometer, or on large length scales, for example, on more than 1 micrometer. Therefore, surface processing can be done at different rates in different areas, for example, inside or outside the proximate region 4, and tapered structures can also be produced.

Enzymes are proteins, which act as catalysts to accelerate chemical reactions between reactants 3. In the vicinity of a surface 1, in a layer of thickness $\leq 1$ μm, for example, stirring and convection may be ineffective, i.e. surface processes are limited by the diffusion of reactants 3 from bulk of a solution to the surface 1. In an embodiment of the present invention, enzymes 2 are used to alter the concentration of reactants 3 in the vicinity of the surface 1 significantly. Advantageously, the enzymes 2 are not altered or consumed during catalysis and typically have a rapid turnover of, for example, several thousands cycles per second.

As discussed previously, in an embodiment of the present invention, enzymes 2 are patterned/deposited on a surface 1 and used to consume or produce chemicals, which react with the surface 1. Well-defined surface-structuring may be achieved by causing the proper interplay between certain parameters. Such parameters include the patterning of the enzymes 2, i.e. position and density, the catalytic turnover of the enzymes 2, the diffusion profile of the reactants 3 and enzymatic products, conditions pertaining to the chemical bath in which an embodiment of the present invention is performed, for example, temperature, pH, salts, etc., the stoichiometry of the reaction taking place between the enzymatic products and the surface 1.

Enzymes 2 are versatile catalysts. They catalyze specific types of reactions and can considerably accelerate reactions, by up to $10^{12}$ compared to non-catalyzed reactions. Additionally, enzymes 2 also have the desired capability of adsorbing/attaching to different types of surfaces 1.

Enzymes are classified based on the type of reaction, which they catalyze. They may also be subdivided into categories according to the Enzyme Commission's system (EC). Many classes of enzymes use or produce chemicals/reactants 3, which can be used for processing surfaces 1. They can be used for etching, for example, if they are strong oxidizers or coordinate oxidized metals, or for depositing materials, for example, if they produce reactants, which can reduce metallic salts from solution. Enzymes 2 can be used to raise or lower the concentration of reactive species, or to change the oxidation state of species in a bath. Some enzymatic reactions, for example involve protons, hydroxides, peroxides, carboxylic acids, amines, or aldehydes. The chemistry of some enzymes from classes EC 1.1, EC 1.2 and EC 1.3 exemplifies that both the synthesis and degradation of aldehydes is possible using enzymes and that a variety of chemical environments, i.e. various co-substrates or cofactors, pH, temperature, etc. can be used. Aldehydes can be used to reduce and deposit metallic ions from solution. Oxidizing aldehydes or reducing chemical species into aldehydes can be used to inhibit or induce the deposition of $Ag^+$ or $Cu^{2+}$ on a surface, respectively.

Enzymes from class EC 1, which are oxydo-reductases are particularly useful for redox reactions. Catalases, EC 1.11.1.6, and peroxidases, EC 1.11.1.7, are enzymes having a rapid turnover, which is up to 650,000 per second for catalase, and approximately 10,000 for some peroxidases, and have the ability to reduce hydrogen peroxide ($H_2O_2$).

In an embodiment of the present invention, localized etching may be done since the reactive species can be generated in the regions of the surface 1 that are desired to be patterned and only small amounts of reactive species accumulate in the chemical bath, which makes the bath safe to handle. Generating a chemical processing environment on a surface locally also potentially prevents other areas from being damaged. Chemical species for processing surfaces which have limited stability can be generated near the areas of the surface where they must react. Therefore, the time needed for diffusion from the enzymatic areas to the processing areas can become shorter than the average lifetime of the enzymatic products. Finally, in contrast to typical etch chemistries, enzymatic activity can be averaged out by diffusion profiles to make local defects unimportant.

Using Enzymes for Protecting Cu

In an embodiment of the present invention, the surface 1 to be patterned was chosen to be copper (Cu). The reactants 3 comprising HCl and $H_2O_2$ were used. The class of enzymes 2 was horseradish peroxidase (HRP). The HRP worked in the presence of HCl and $H_2O_2$, as long as the pH was higher than 2.5. The concentration of $H_2O_2$ that was used was approximately 0.04 M since $H_2O_2$ is an inhibitor of peroxidases when it is at too high a concentration.

In the present embodiment, HRP reduced $H_2O_2$ in an acidic bath of HCl and in the presence of ABTS, 2,2'-azino-bis(3-ethylbenzthiazoline-6-sulphonic acid), to lower the concentration of $H_2O_2$ in the regions of the surface where the enzymes were patterned. ABTS is an electron donor for the reduction of $H_2O_2$; it is a co-substrate for HRP. Enzymatic activity resulted in the oxidation of ABTS, which then colored, the coloring being useful in indicating the occurrence of enzymatic activity in the bath. Entries in the encyclopedia of enzymes as found at http://www.chem.qmul.ac.uk/iubmb/enzyme/speculate that $H_2O_2$ can be reduced without the need for an electron donor. This mechanism would be based on the dismutation of $H_2O_2$ into water and oxygen and might be useful to etch Cu, for example, without the need for ABTS or an electron donor.

The HRP enzymes were micro-contact printed onto a Cu layer. The Cu was 50 nm thick and electron-beam deposited on the native oxide of a silicon wafer. The HRP enzymes were dissolved in a phosphate buffered saline solution, pH 7.4, typically to a concentration ranging from 1 mg mL$^{-1}$ to 20 μg mL$^{-1}$. The solution was used to cover a poly(dimethylsiloxane) (PDMS) stamp, which was patterned by replication of a lithographically-prepared mold. The stamp covered with the solution of HRP was placed in a petri-dish for approximately 30 minutes. During this inking step, HRP enzymes adsorbed spontaneously to the surface of the stamp. The stamp was then rinsed using with buffer, de-ionized water, and it was then dried using nitrogen. The stamp was placed by hand onto the Cu surface for a few seconds, typically 5 seconds, before it was removed. The stamp could also be applied using a mechanical printing tool if overlay alignment of the enzyme patterns with patterns already present on the surface is desired.

In the present example, the enzymes were patterned onto $2\times 2$ µm² square areas, which were grouped in approximately $80\times 30$ µm² rectangles. The square areas in each rectangle had a separation distance of approximately 5 µm and formed a quadratic lattice. After 20 minutes in the etch bath, the Cu layer outside of the rectangles was removed. There, the enzymes did not protect the Cu by reducing $H_2O_2$. Inside the rectangles, the Cu in between the square areas was etched incompletely as a result of the lower $H_2O_2$ concentration. Inside the square areas, the Cu was totally protected.

Using Enzymes for Etching Cu

Etching a metal can be done by having a strong oxidizer and a complexing ligand in a bath as disclosed by Geissler et. al in Langmuir, 2003, volume 19, pages 6567 to 6569. A compound having a nitro-functional group and polyethyleneimine (PEI) can be used at pH 9 to etch Cu. Such a bath is not stable for more than a few days and its preparation is dangerous as it requires the addition of large quantities of HCl for lowering the pH of the initial solution of PEI. Here, PEI is a complexing ligand for oxidized Cu and ensures that the oxidized Cu becomes soluble and can diffuse from the surface to the bath.

An embodiment of the present invention can be used for generating complexing ligands for oxidized metals using enzymes. Enzymes, which catalyze the formation of amines, such as, for example, lyases, ligases, can be used. In particular, different types of enzymes can be used to cleave peptides to generate amino acids. In this case, an etch bath would contain a precursor for amines and not directly amines. Advantageously, such baths would be safer and simpler to prepare than would be the case for baths prepared for previously-proposed surface-processing techniques.

Using Enzymes for Depositing or Preventing the Deposition of Materials

Enzymes on surfaces can also be used to induce or prevent the deposition of chemical species from a bath by making them insoluble, reactive for cross-linking with a chemical already present on a surface, or by reducing them. A preferred possibility is to use enzymes on a surface for electroless deposition processes (ELD). In ELD, an oxidized metallic complex and a reducing agent are present in a bath and the spontaneous reduction of the metal by the reducing agent, although thermodynamically favorable, is kinetically inhibited. This inhibition is typically done by complexing the metal complex with strong ligands. A catalyst on a surface is needed to start the reduction reaction and the deposition of the reduced metal on the surface. In ELD, metals are deposited from solution on insulating substrates in the regions of the surface where a catalyst has been patterned. Catalysts for ELD are typically Pd-based particles or metal particles as described in the book *Electroless Plating: Fundamentals and Applications*; Mallory, G., Hajdu, J. B., Eds.; American Electroplaters and Surface Finishers Society: Orlando, Fla., 1990. A catalyst is needed only to start the ELD process, which then proceeds autocatalytically. Aldehydes such as formaldehyde are frequently used as reducing agents, in particular for the ELD of Cu.

In an embodiment of the present invention, enzymes patterned on a surface can be used to vary locally the concentration of reducing agent on a surface. Aldehydes can be generated in the areas of a surface where enzymes are patterned to reduce metals such as $Cu^{2+}$ or $Ag^+$. Alternatively, enzymes can be used to oxidize aldehydes to prevent the ELD of Ag and Cu, for example. Additionally, enzymes on a surface can be used to modify the ligands of the metal complex.

Continuous Features and Averaged Enzymatic Activity on a Surface

In an embodiment of the present invention, the geometry of the enzyme pattern on the surface, the diffusion characteristics of the substrates and products, the rate of etching or deposition, and the rate of enzymatic activity in combination define the surface concentration of the various reactants involved in the processing of the surface. Advantageously, in an embodiment of the present invention, enzymatic activity on a surface can be averaged out by diffusion patterns. Homogeneous protection can be achieved without needing perfect coverage of enzymes in the patterned regions. The presence of inactive enzymes on a surface is unimportant as long as the average enzymatic activity per unit area on a surface is sufficient. In addition, continuous patterns can be formed using an array of enzymatic sites provided that the concentration profile of the enzymatic products is sufficient to affect the processing of the surface at any point in between adjacent enzymatic areas.

Gradients and One Enzyme Pattern for Many Patterns of Material

Advantageously, a single pattern can be used to create multiple patterns of etched or protected material using different bath chemistries. For example, by changing the etch strength of the bath for a given enzymatic surface activity, the gradient profile of the enzymatic products in the bath can be shortened or lengthened. This results in transferring the enzymatic pattern into the material with a reduced or increased lateral size. Because designing patterns in molds, stamps, or optical masks is costly and takes time, it is desirable to have a process that can use one main pattern for generating a variety of final patterns in a material. This might be of particular interest for producing optical elements having light-diffracting structures because the dimensions of the pattern depend on the wavelength of the light to be diffracted. The width of parallel lines can be modulated by varying the strength of a bath rather than by having to redesign a new mask of mold.

Enzymes can be patterned on a surface with varying density. This can be done for example by depositing enzymes on a surface using inkjet technology. Multiple nozzles each having an ink with a different concentration of enzyme can be used. Regions having different enzyme density can be used to create different processing rates in different regions of a surface. Various etch rates can be simultaneously achieved, for example, and structures with various tapers can be formed. Structures having different heights or depths can also be formed in a manner similar to grayscale photolithography, where the duration of exposure of a photoresist to light defines the depths of the resulting etched structures. Grayscale lithography processes are however very sensitive to process parameters, exposure duration, development time, etc. whereas patterning enzymes with varying surface density is comparatively simpler.

Any of the steps of an embodiment of the present invention can be performed in parallel or without maintaining a strict order of sequence.

The present invention has been described above purely by way of example and modifications of detail can be made within the scope of the invention.

Each feature disclosed in the description, and, where appropriate, the claims and the drawings may be provided independently or in any appropriate combination.

The invention claimed is:

1. A method for processing a surface comprising the steps of:
   depositing at least one class of enzymes onto the surface;
   introducing at least a reactant into an environment of the surface, and causing interaction between the enzymes and the reactant, thereby to cause processing of a region of the surface, the processed region of the surface being defined with respect to a region of the surface proximate to where the enzymes have been deposited, wherein the surface is selected to comprise copper (Cu), the reactants are selected to comprise hydrochloric acid (HCl) and hydrogen peroxide ($H_2O_2$) and the class of enzymes is selected to comprise horseradish peroxidase (HRP).

2. A method as claimed in claim 1 wherein processing of the surface comprises one of: etching of the surface and deposition of at least a depositing species on the surface.

3. A method as claimed in claim 1 wherein, in the step of causing interaction between the enzymes and the reactant, the processed region of the surface is substantially outside the proximate region.

4. A method as claimed in claim 1 wherein, the spatial extension of the proximate region relative to where the enzymes have been deposited on the surface is adjustable by adjusting the concentration of the reactant, the density of the enzymes, the temperature of the environment of the surface or a combination thereof.

5. A method as claimed in claim 1 wherein, in the step of depositing the enzymes, at least another class of enzymes is additionally deposited on the surface.

6. A method as claimed in claim 1 wherein, in the step of depositing the enzymes, the enzymes are deposited onto the surface by micro-contact printing.

* * * * *